United States Patent
Las Navas Garcia

(10) Patent No.: US 7,048,888 B2
(45) Date of Patent: May 23, 2006

(54) AUTOMATIC COVER SYSTEM FOR PROXIMATE ANALYZERS AND THE LIKE

(76) Inventor: Jose Maria Las Navas Garcia, Parque Infantas, chalet 150, Valdomorillo (ES)

(*) Notice: Subject to any disclaimer, the term of this patent is extended or adjusted under 35 U.S.C. 154(b) by 1221 days.

(21) Appl. No.: 09/894,591

(22) Filed: Jun. 28, 2001

(65) Prior Publication Data

US 2003/0003016 A1    Jan. 2, 2003

(51) Int. Cl.
    *G01N 31/12*   (2006.01)
(52) U.S. Cl. .............. 422/64; 422/78; 422/99; 422/102
(58) Field of Classification Search ............... 422/64, 422/78, 99, 102
    See application file for complete search history.

(56) References Cited

U.S. PATENT DOCUMENTS

| | | | |
|---|---|---|---|
| 4,238,450 A | 12/1980 | Bredeweg et al. | |
| 4,294,126 A | 10/1981 | Tomoff et al. | |
| 4,303,615 A | 12/1981 | Jarmell et al. | |
| 4,455,280 A * | 6/1984 | Shinohara et al. | 422/63 |
| 4,522,788 A | 6/1985 | Sitek et al. | |
| 4,539,645 A | 9/1985 | Krottinger et al. | |
| 4,639,179 A | 1/1987 | Soulard | |
| 4,721,549 A | 1/1988 | Bogenschutz et al. | |
| 4,952,108 A | 8/1990 | Weigand et al. | |
| 5,045,476 A * | 9/1991 | Huber | 436/81 |
| 5,064,009 A | 11/1991 | Melcher et al. | |
| 5,077,013 A * | 12/1991 | Guigan | 422/64 |
| 5,266,118 A * | 11/1993 | Mitra | 118/726 |
| 5,298,196 A * | 3/1994 | Heung | 588/16 |
| 5,341,854 A | 8/1994 | Zezulka et al. | |
| 5,382,884 A | 1/1995 | Hussami | |
| 5,395,586 A | 3/1995 | Hemzy et al. | |
| 5,906,857 A | 5/1999 | McKee et al. | |
| 5,976,263 A * | 11/1999 | Poole | 118/726 |
| 6,015,532 A | 1/2000 | Clements et al. | |
| 6,117,391 A | 9/2000 | Mootz et al. | |

* cited by examiner

Primary Examiner—Jan M. Ludlow
(74) Attorney, Agent, or Firm—Bazerman & Drangel PC

(57) ABSTRACT

An apparatus is provided to automatically cover and uncover crucibles according to a predetermined procedure in a proximate analyzer. A series of crucibles mounted in a first carousel is heated in a furnace. A second carousel mounted above the first carousel holds crucible covers. A mechanism synchronizes the movements of the carousels so that the heated crucibles are automatically covered and uncovered at the appropriate times during the analysis with a corresponding cover by lowering or raising the second carousel. The movements of both carousels are automatically controlled so that at appropriate points in the testing cycle they rotate simultaneously about a common central axis and a crucible is deposited on a weighing platform by controlling the vertical motion of the entire carousel apparatus. The crucible is weighed either with or without a crucible cover depending on the stage of the analysis without the need of manual intervention.

29 Claims, 8 Drawing Sheets

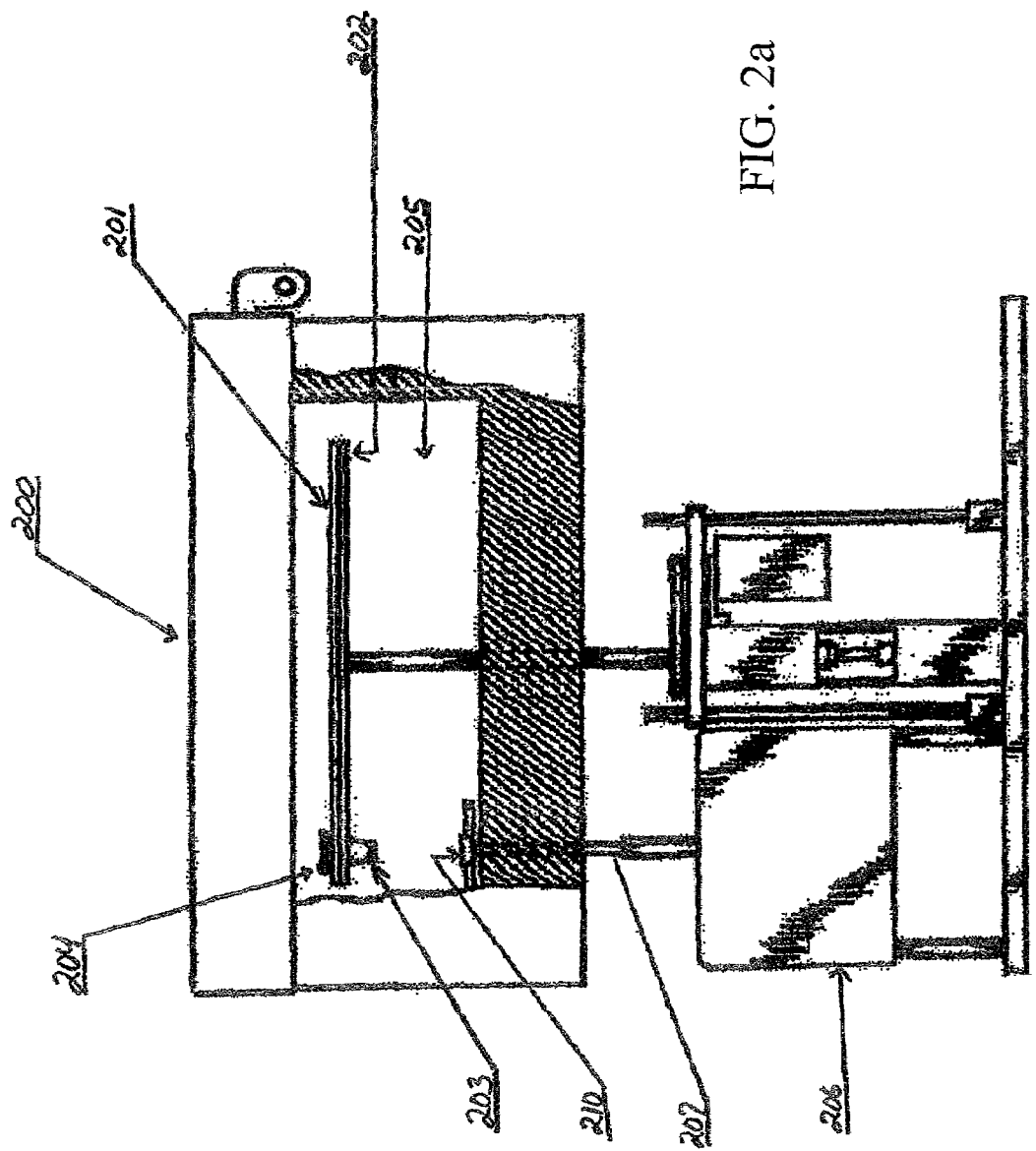

AUTOMATIC COVER SYSTEM FOR PROXIMATE ANALYZERS AND THE LIKE

BACKGROUND OF THE INVENTION

The present invention relates to the automation of proximate analyzers and the like, and more particularly, to apparatus and a method for opening and closing crucibles during such analysis.

Systems for proximate analysis of fossil fuels such as coal and coke through the use of heat are well known. The samples are subject to a heating and cooling cycle in a furnace chamber. The samples are in crucibles. The crucibles are in turn seated on a platter or carousel positioned within the chamber. At various times during the cycle the crucibles are covered or uncovered through the placing or removal of crucible covers. A weighing platform is positioned within the furnace chamber. The carousel continuously deposits the crucibles in a predetermined sequence on the weighing platform and the weights of the crucibles monitored to calculate the contained volatiles based on weight loss during heating.

U.S. Pat. No. 4,522,788, to Sitek et al., issued on Jun. 11, 1985, is directed to such a system. In this patent, the crucibles are placed manually on a carousel and covered and uncovered manually during the analysis. The crucibles are uncovered for initial weighing and then heated in nitrogen atmosphere to remove moisture content from the samples in them, the covers are then remounted by hand and the crucibles are heated to a higher temperature also in a nitrogen atmosphere to obtain volatiles, cooled, removed by hand in the presence of nitrogen atmosphere and heated again in oxygen atmosphere to obtain ash. In order to make such analyses more efficient and safer there is a need for a proximate analysis system that can automatically cover and uncover a series of crucibles at the appropriate stages of the analysis without requiring manual intervention.

SUMMARY OF THE INVENTION

The present invention meets the foregoing needs by use of a second upper carousel sharing a common axis with the original lower carousel. The crucibles are mounted in openings on the lower carousel and the crucible covers are mounted in openings on the upper carousel. The lower carousel is used solely for the manipulation of the crucibles and the upper carousel for the manipulation of the crucible covers. The carousels both rotate and move up and down along their central axis. The movements of both carousels are coupled so as to simultaneously move around their central axis but move independently along their common vertical axis.

At appropriate points in the testing cycle, individual crucible are automatically deposited on a weighing platform through vertical motion of the entire dual carousel apparatus. The presence or absence of a crucible cover during weighing is determined by the vertical motion along the common axis of the upper carousel. Two pneumatic cylinders control the vertical movement of the carousels. The first pneumatic cylinder acts to raise and lower the dual carousel mechanism so that a crucible is deposited on the weighing platform and a second pneumatic cylinder act to raise and lower the upper carousel in relation to the lower carousel. When the vertical movement of the upper carousel is such as to bring the upper and lower carousel together, the crucible covers rest on, and seals the crucibles, during heating, or weighing. When the upper carousels are separated, the crucible is uncovered and open to the atmosphere during heating and weighing. Thus, in the cycle, the carousels will automatically act to remove the covers during heating to remove moisture, remount the covers to obtain volatiles and remove the covers to obtain ash.

BRIEF DESCRIPTION OF THE DRAWINGS

FIG. 2A is a schematic drawing showing the present invention with the view having a partial cut out of the furnace chamber showing the two carousels together in heating mode.

DETAILED DESCRIPTION OF THE INVENTION

Figure 1:
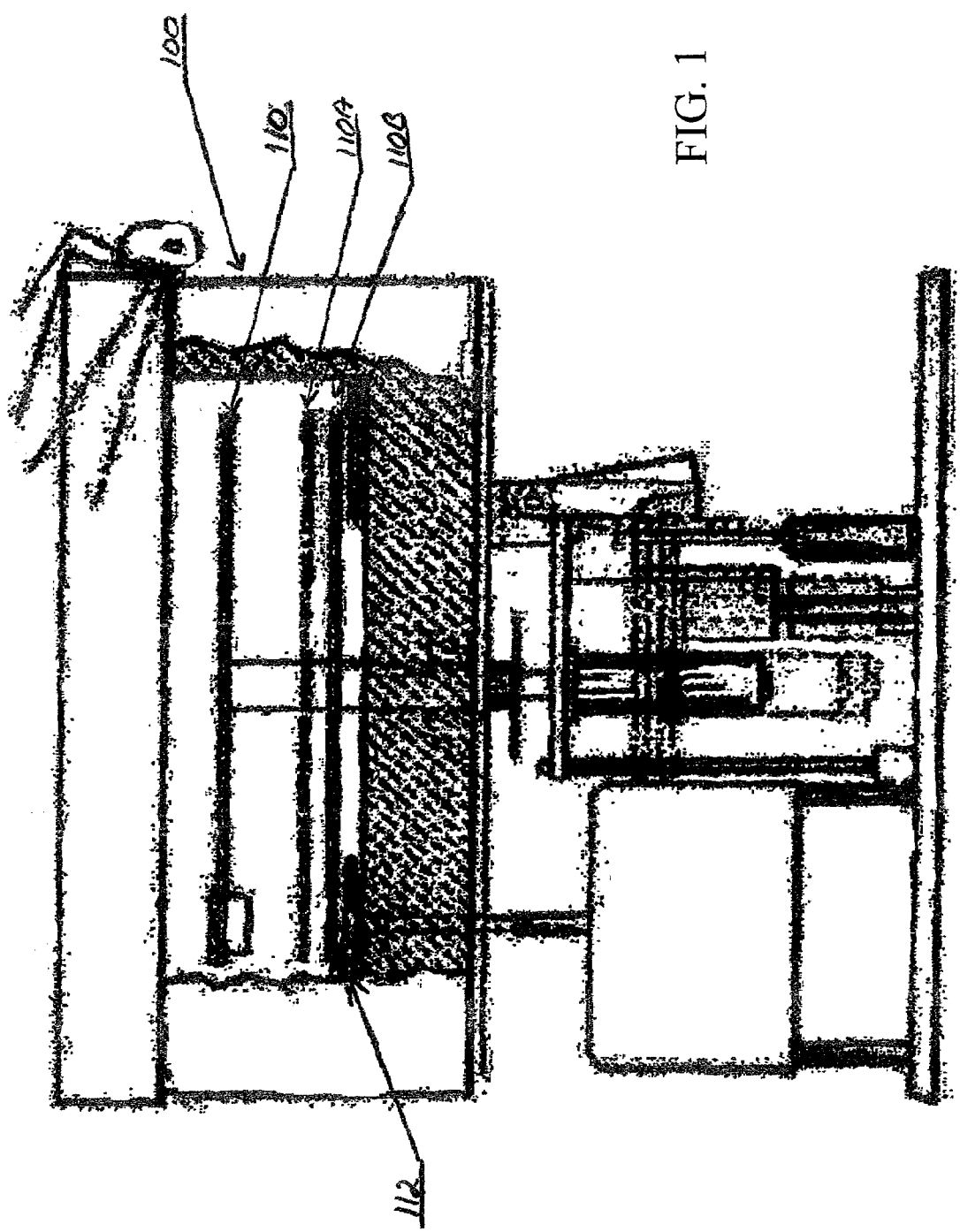
FIG. 1 is a schematic drawing showing a prior art proximate analyzer.

FIG. 1 is a schematic partial cut away view of a prior art proximate detector 100 showing the interior of the furnace chamber. As can be seen in the drawing, there is one carousel 110 which is capable of holding multiple crucibles. The carousel is capable of moving up and down to positions 110A and 110B to heat a crucible and place a crucible on a weigh platform 112 for weighing. At different stages in the heating process, it may be necessary to place a cover on certain crucibles. According to the prior art scheme, such placement of covers is performed manually on each crucible.

FIG. 2A shows improved proximate analyzer 200 of the present invention in the same view as prior art analyzer shown in FIG. 1. The present invention differs in that there are two carousels in the furnace chamber 205. Upper carousel 201 carries and transports crucible covers exemplified by crucible cover 204 while lower carousel 202 carries and transports crucibles exemplified by crucible 203. When carousel 201 and carousel 202 are brought together a cover 204 is placed on a crucible 203.

Figure 2B:
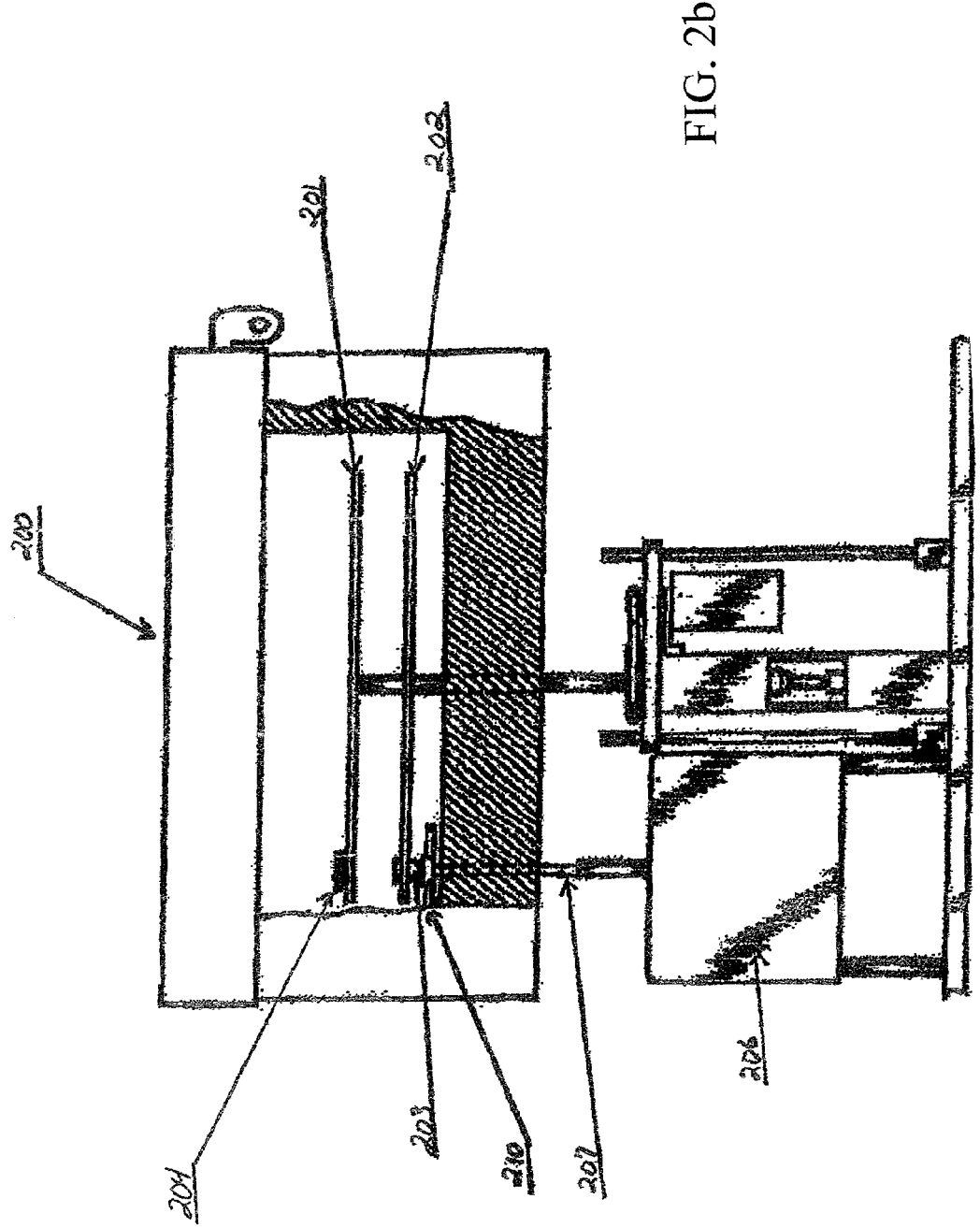
FIG. 2B is a schematic drawing showing the present invention with the view having a partial cut out of the furnace chamber showing the two carousels apart in weighing mode.

FIG. 2B shows the position of carousels 201 and 202 at a point in the analytical cycle where a crucible 203 is weighed uncovered. Lower carousel 202 is in its lowered position allowing a crucible 203 to be placed on the balance platform 210 while crucible cover 204 is retained above and separated from a crucible 203 by upper carousel 201 during weighing on a balance 206.

Figure 2C:
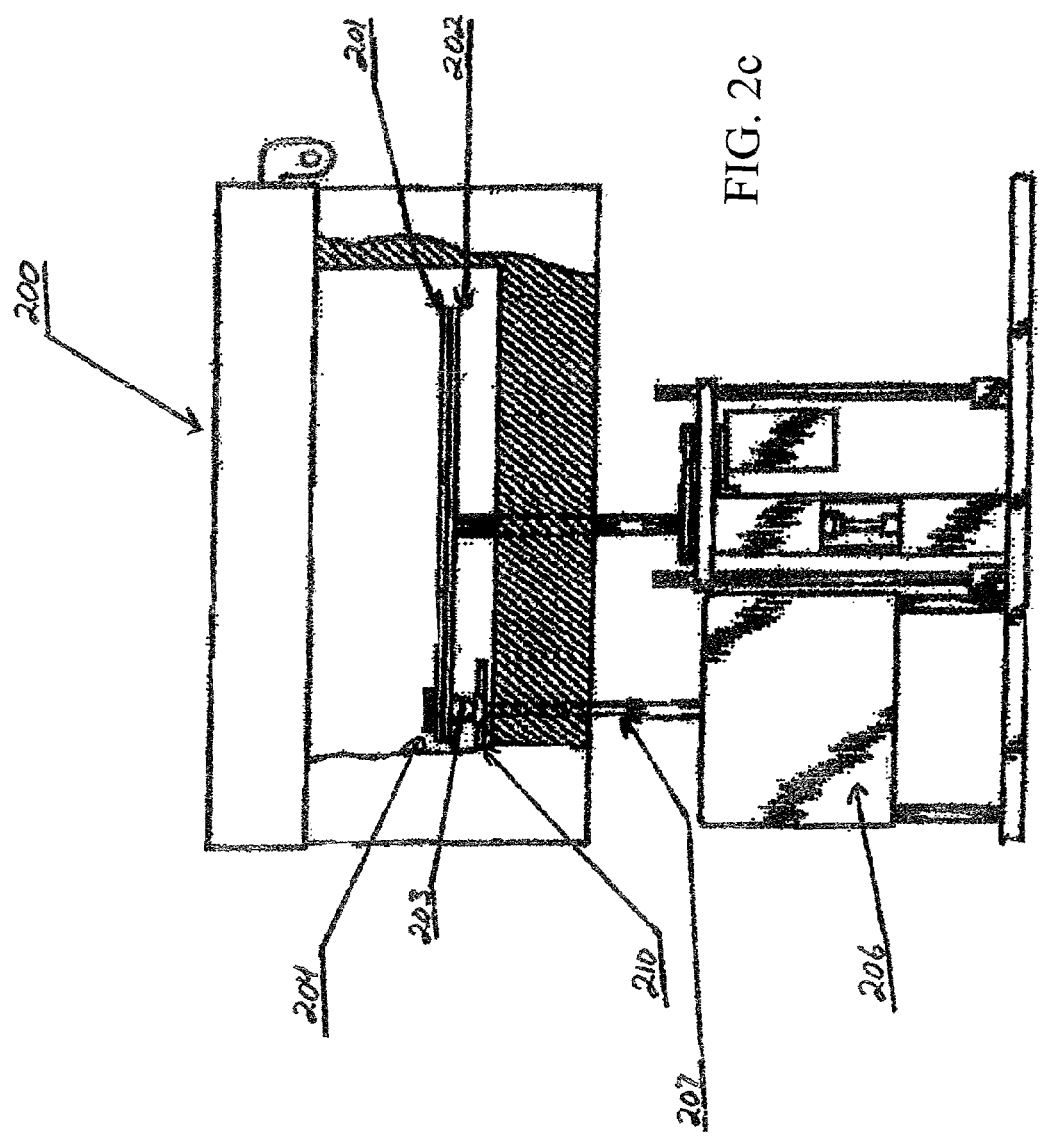
FIG. 2C is a schematic drawing showing the present invention with the view having a partial cut out of the furnace chamber showing the two carousels together and the covered crucible in weighing mode.

FIG. 2C shows both the lower carousel 202 and upper carousel 201 lowered allowing a crucible 203 to have a cover 204 on it while being weighed on the balance 206.

Figure 3:
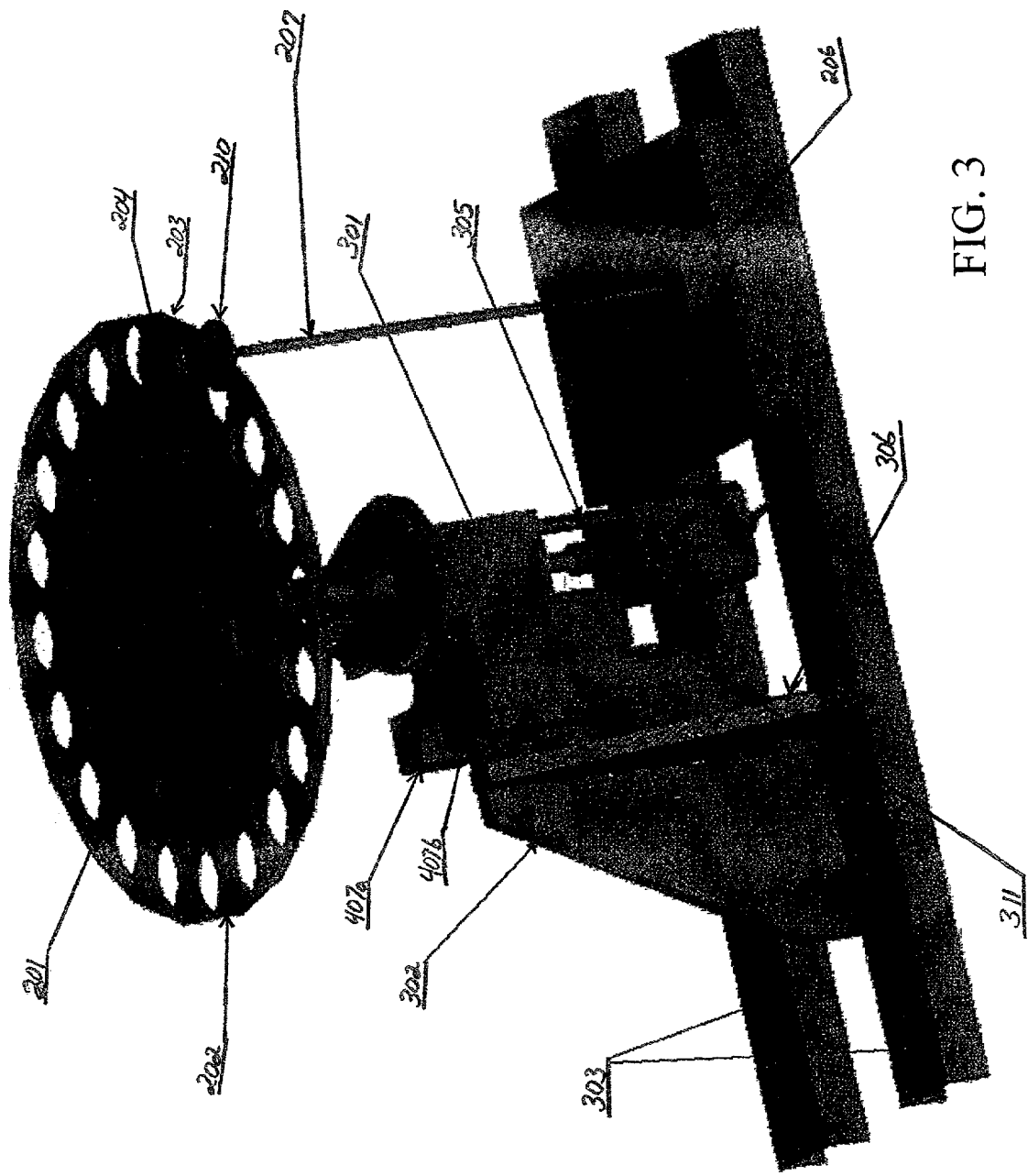
FIG. 3 is a tilted front perspective view of the present invention showing its attachment to a support structure.
Figure 4:
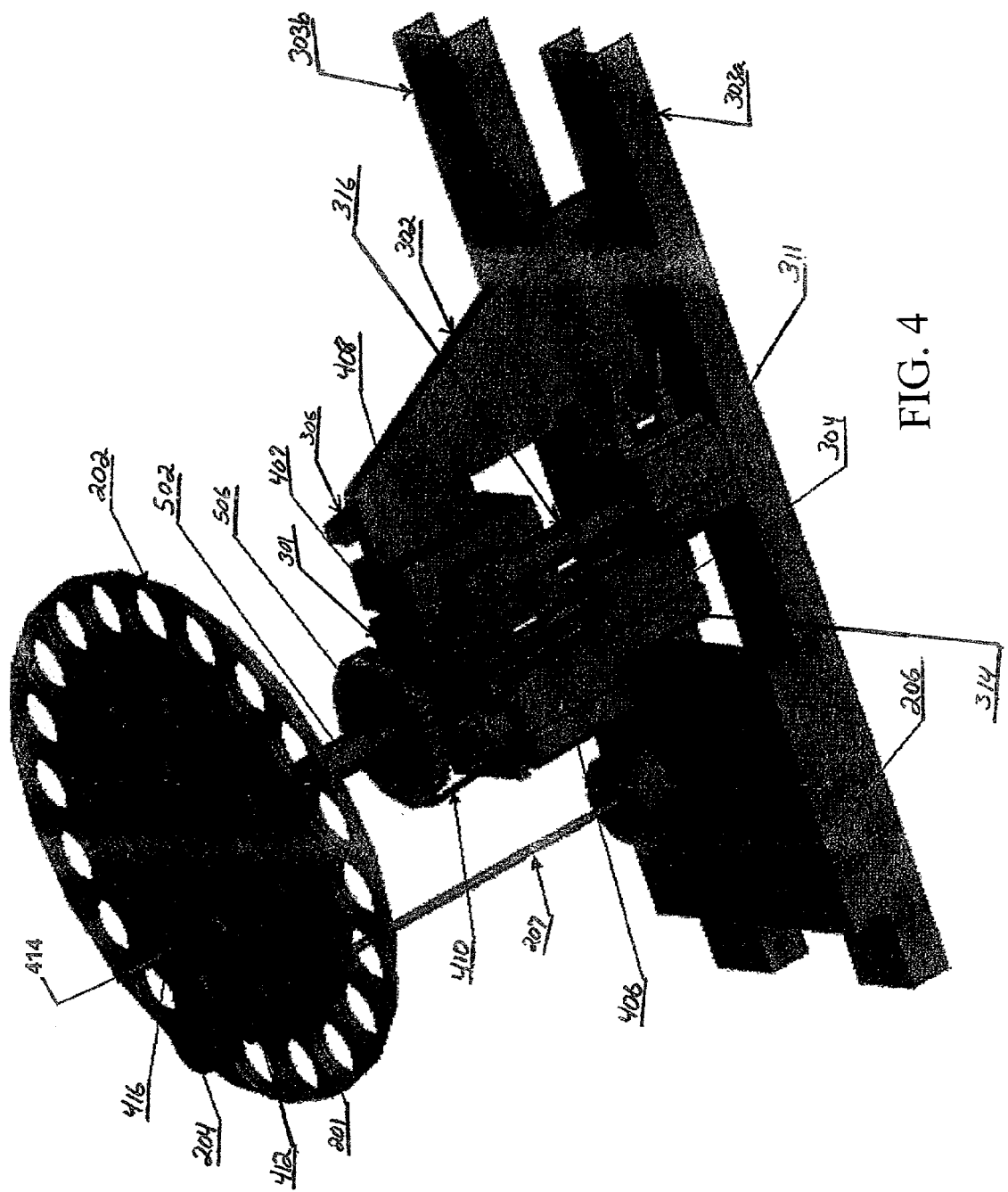
FIG. 4 is a tilted back perspective view of the present invention showing its attachment to a support structure.
Figure 5:
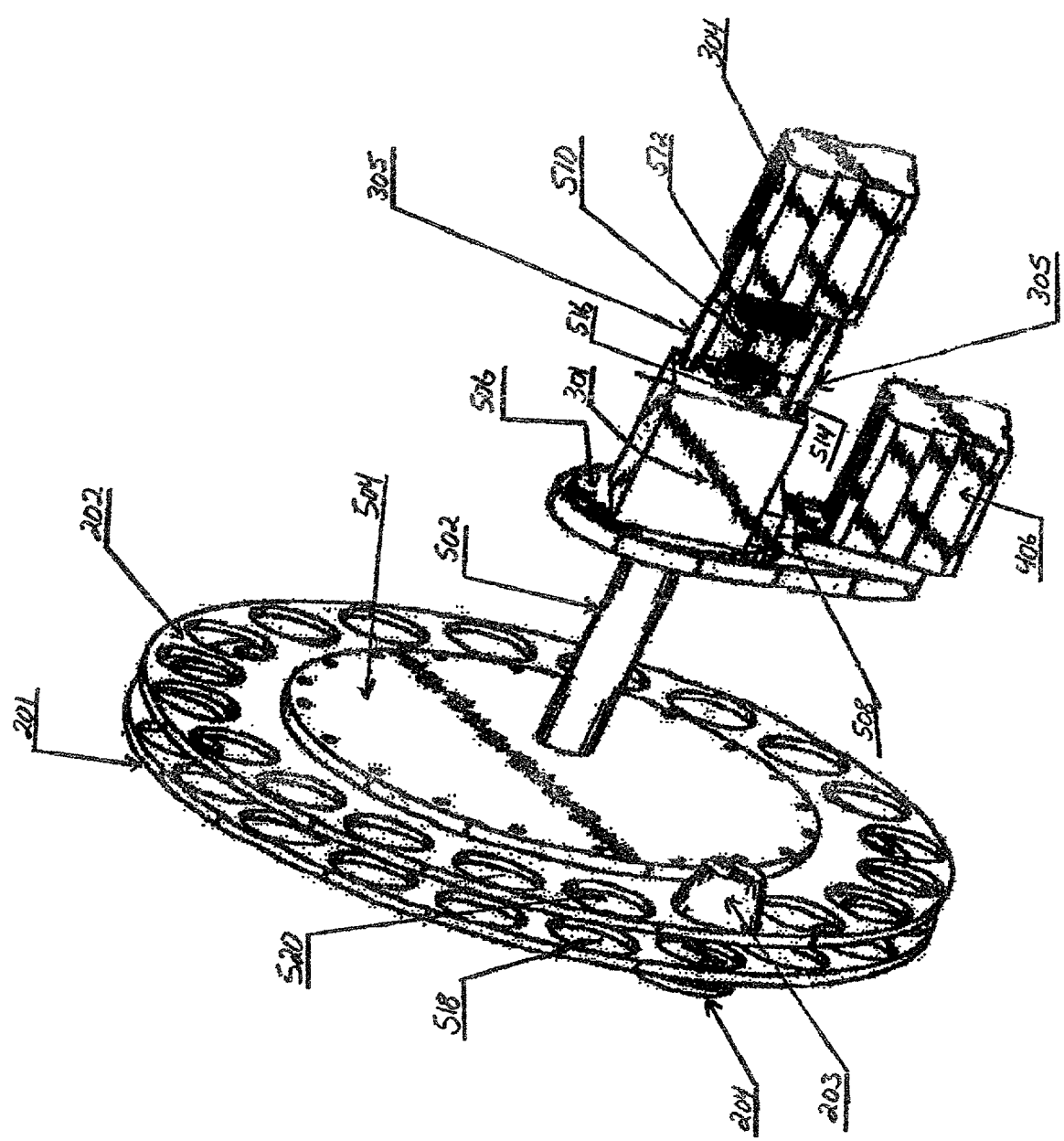
FIG. 5 is a perspective view of the dual carousel mechanism without its support structure tilted on its side.

The detailed mechanism of the present invention may be understood by reference to FIG. 3 which is a tilted front perspective top view, FIG. 4 which is a tilted back perspective top view of the present invention with both the upper carousel 201 and lower carousel 202 in the closed position and FIG. 5 which is a view of the dual carousel system without a support structure tilted on its side to show its components. The furnace chamber which forms a part of the proximate analyzer is not shown in these drawings.

The mechanism is supported by a base 303 which, in the present embodiment, is comprised of two beams 303a and 303b that hold the system components including balance 206. Arm 302 attached to base 303 and supported by a brace 306 is connected to component 407a of a slide joint 407, and component 407b of slide joint 407 is connected to body 301 which supports the dual carousel mechanism and which moves up and down along slide joint 407, better seen in FIG. 4, to place crucibles 203 on balance platform 210 connected to balance 206 by means of shaft 207. The space between the two beams of base 303 allows room for the upper carousel pneumatic cylinder 304 to move up and down between the beams when both the carousels are lowered onto the balance platform 210.

The body 301 is connected to an elevation block 314 as seen in FIG. 4. The connection between the elevation block 314 and the main support arm 302 is accomplished through a slide joint 407 which allows the dual carousel system to move up and down along the main support arm 302. The combination of body 301 which is connected to elevation block 314 which is in turn connected to elevation shaft 316 projecting from pneumatic cylinder 311 supports the weight of the entire dual carousel mechanism. Pneumatic elevation cylinder 311 mounted on base beam 303a raises and lowers the entire dual carousel mechanism. Although pneumatic means are preferred, any other means known in the art to raise or lower a structure such as worm gears or pulley arrangements may be used to control the vertical movement of the entire dual carousel mechanism.

The carousels themselves can be made from any rigid material that can withstand elevated temperatures without substantial deterioration or distortion, preferably metallic sheet materials such as stainless steels, and any other such materials used in the art. As seen in FIG. 5 upper carousel 201 has openings 518 to accommodate crucible covers 204 and lower carousel 202 has openings 520 to accommodate crucibles 203.

As seen most clearly in FIG. 5 a retainer 514 is connected to shaft 502 which fixes the position of hollow shaft 502 between two bearings (not shown) one on each side within body 301 so that when moving upper carousel shaft 510 up for removal of crucible covers shaft 502 will not be shifted or dragged up relative to body 301 around the upper carousel shaft 510. In addition, in the present embodiment, a screw 516 protrudes from retainer 514 that serves to activate a magnetic sensor producing a signal indicating the horizontal rotational position of the carousels thereby enabling the position of each crucible to be tracked by a computer program that monitors the analysis and calculates weight loss at each stage. As will be apparent to those skilled in the art, other means of tracking the position of the carousels may be used such as reflective tape affixed to shaft 502 which in conjunction with a light source sends a signal to an appropriate sensor.

As most clearly seen in FIG. 5, the lower carousel 202 is attached to a hollow shaft 502 by means of small disk 504 which is attached to the bottom of lower carousel 202 by attaching means known in the art such as riveting welding and the like. Hollow shaft 502 is connected to a gear 506 at the end distal to small disk 504. An opening (not shown) at the center of small disk 504 and lower carousel 202 allows passage of shaft 510 which is connected to upper carousel 201. The lower carousel 202 is turned using a step motor 406 which has a pulley 408 connected to the drive shaft of step motor 406. The pulley 408 is connected to the gear 506 with a belt 410. The step motor 406 is connected to the main body 301 using a motor support 508 most clearly seen in FIG. 5. While the step motor 406 directly controls the rotation of the lower carousel 202, there is no motor which independently turns the upper carousel 201. Any other suitable means known in the art may be used to drive the rotation of lower carousel 202. Movement of upper carousel 201 is achieved via a synchronization pin 414 which is screwed into the upper face of lower carousel 202 and protrudes through the upper face of upper carousel 201 via keyhole 416 thereby synchronizing the rotation of the carousels. Synchronization pin 414 is sufficiently long so that it remains within keyhole 416 when upper carousel 201 is raised during normal operation of the analyzer.

Upper carousel 201 is connected to a solid shaft 510 which then passes through the hollow shaft 502 of the lower carousel 202 and is then connected to the piston shaft (unseen) from upper carousel pneumatic cylinder 304 via a rotational coupling 512 to accommodate the rotational motion imparted by gear 506. The connection of the upper carousel 201 to the end of shaft 510 distal from pneumatic cylinder 304 is made by using a central screw 412 although other fastening means known in the art may be used. As is known in the art, a screw connects the rotational coupling 512 and the piston shaft of pneumatic cylinder 304 to allow the rotational coupling 512 to rotate freely while the screw is fixed to the pneumatic cylinder 304. The shaft 510 for upper carousel 201 is fixed to the rotational coupling 512 thereby allowing carousel 201 to rotate while being raised or lowered by pneumatic cylinder 304. Pneumatic cylinder 304 is connected to the main body 301 using support columns 305.

The vertical movement of upper carousel 201 is controlled by pneumatic cylinder 304 via carousel shaft 510. Although pneumatic means are preferred, any other means known in the art to raise or lower a structure such as worm gears or pulley arrangements may be used to control the vertical movement of upper carousel 201. By lowering carousel 201, crucible 203 is covered with crucible cover 204 while by raising carousel 201 crucible cover 204 is removed from crucible 203.

Figure 6A:
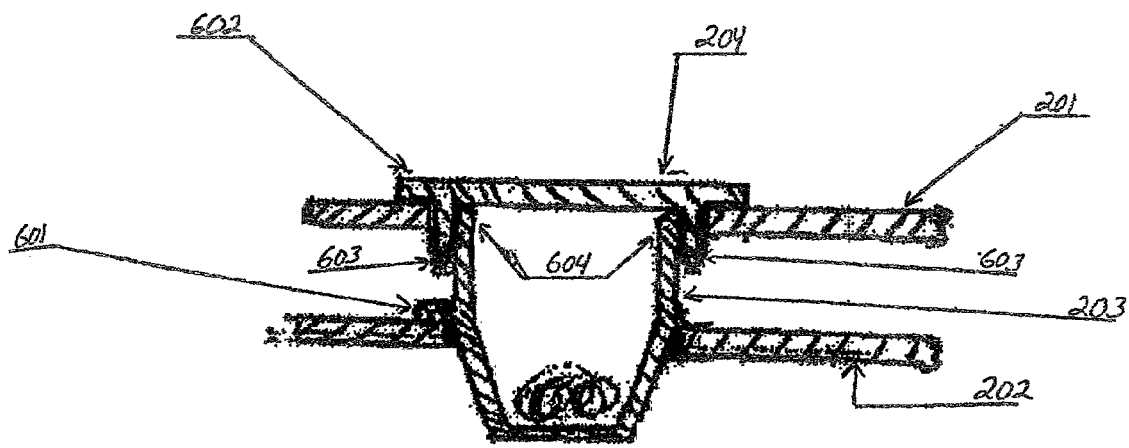
FIG. 6A is a cross-sectional drawing of a segment of the dual carousel system in closed position showing a crucible containing a sample seated in a carousel covered with a crucible cover seated in the upper carousel.
Figure 6B:
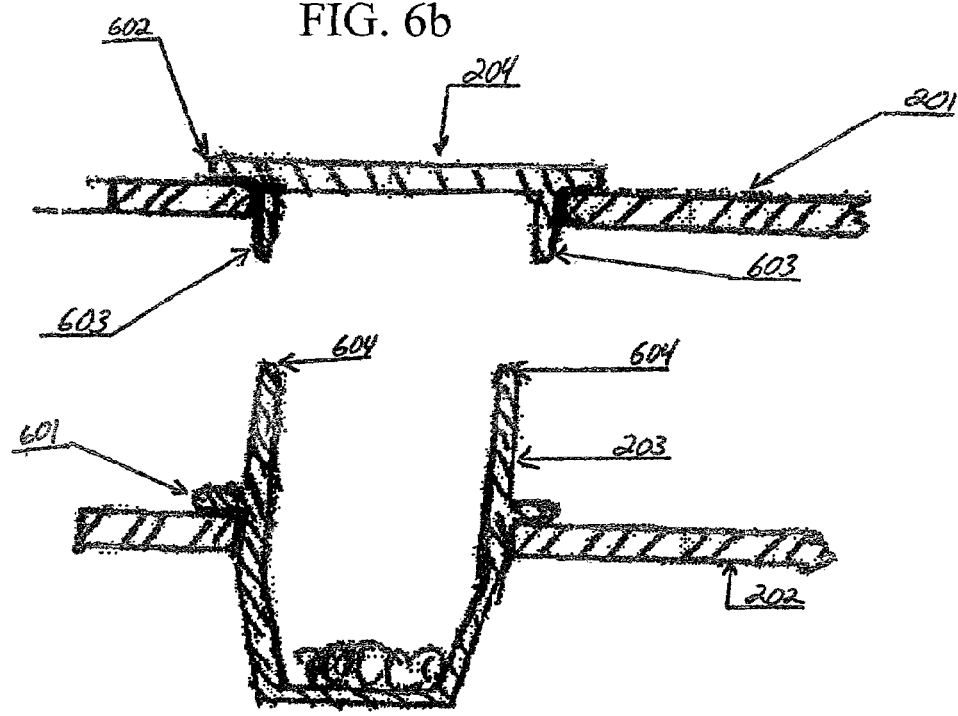
FIG. 6B is a cross-sectional drawing of a segment of the dual carousel system in open position showing an uncovered crucible containing a sample seated in a carousel and the crucible cover seated in the upper carousel raised up to uncover the crucible.

FIG. 6A is a cross-sectional schematic drawing of a crucible 203 seated within an opening 520 of lower carousel 202 that is closed with crucible cover 204 which is seated within an opening 518 of upper carousel 201 when the carousels are in the closed position. FIG. 6B is a cross-sectional schematic drawing of a crucible 203 seated within an opening 520 of lower carousel 202 and a crucible cover 204 which is seated within an opening 518 of upper carousel 201 when the carousels are in the open position. As seen in FIG. 6A the crucible 203 has a ledge 601 around its exterior perimeter with the ledge located in the upper portion of the crucible. The maximum diameter of crucible 203 exclusive of ledge 601 relative to opening 520, which is preferably a circular opening, is such that crucible 203 fits relatively loosely within opening 520 and ledge 601 rests on the surface of carousel 202. To facilitate this, the lower portion of crucible 203 beneath ledge 601 may be a conical segment. Under the aforesaid circumstances with the crucible cover 204 raised, as shown in FIG. 6B and FIG. 2B, crucible 203 will be supported only by balance platform 210 when the dual carousel mechanism is lowered sufficiently via pneumatic cylinder 311 as the loose fit permits carousel 202 to drop below supporting crucible ledge 601. Balance 206 will therefore register the actual weight of crucible 203 plus the weight of any contents.

Similarly, crucible cover 204 has ledge 602 around its exterior perimeter with the ledge located at the top of the cover. As shown in FIG. 6A crucible cover 204 has a lip 603 that fit over the rim 604 of crucible 203 to cover it. Preferably, lip 603 tapers to facilitate fitting over rim 604 of crucible 203. The maximum diameter of crucible cover 204 exclusive of ledge 602 relative to opening 518, which is preferably a circular opening, is such that crucible cover 204 fits loosely within opening 518 and ledge 602 rests on the surface of carousel 201. Under the aforesaid circumstances with the crucible cover 204 lowered, as shown in FIG. 6A, and FIG. 2C crucible 203 covered by crucible cover 204 will be supported only by balance platform 210 when the dual carousel mechanism is in the closed position and is lowered sufficiently via pneumatic cylinder 311, as the loose fit permits lower carousel 202 to drop below supporting crucible ledge 601 and upper carousel 201 to drop below supporting ledge 602 so that crucible cover 204 rests only on crucible 203 which stands freely on balance platform 210. Balance 206 will therefore register the actual weight of crucible 203 plus the weight of crucible cover 204 plus the weight of any contents.

Crucible 203 and crucible cover 204 may be fabricated of any materials commonly used in the art, such as thermally stable and durable ceramic compositions and metals.

The carousels of the present invention are designed to operate within a furnace as schematically depicted in FIGS. 2A, 2B and 2C. When the mechanism is operated with the covers off or in an open position, the processes that occur to raise carrousel 201 are as follows: the piston of pneumatic cylinder 304 pushes rotational coupling 512 up, pushing shaft 510 up through hollow shaft 502. This, in turn, pushes upper carousel 201 up, thereby separating it from lower carousel 202 and carrying crucible covers 204 away from crucibles 203. When pneumatic cylinder 311 lowers the dual carrousel mechanism so that crucible 203 touches balance platform 210. The distance between the carousels is adjusted so that it is great enough to keep crucible 203 out of contact with either the upper carousel 201 or crucible cover 204.

When the mechanism is operated with the covers on or in a closed position, the processes that occur to lower carrousel 201 are as follows: the piston of pneumatic cylinder 304 pulls rotational coupling 512 down pulling shaft 510 down through hollow shaft 502 and pulls upper carousel 201, to which shaft 510 is connected, down to bring it together with lower carousel 202 so that covers 204 on carousel 201 are placed on crucibles 203 on carousel 202. When pneumatic elevation cylinder 311 goes down, crucible 203, covered with cover 204 will be deposited on balance platform 210.

The advantages of the improvement of the present invention may be understood by comparison with the prior art. A proximate analysis including a cycle for moisture, volatiles and ash using the prior art analyzer of U.S. Pat. No. 4,522,788 requires the following steps: obtaining the tare weight of the crucibles, introducing sample to all crucibles, reweighing to obtain sample weight, heating the furnace, reweighing to obtain moisture content, opening the furnace door and manually covering the crucibles, closing the furnace and ramping the temperature higher to obtain volatiles, cooling the furnace down, opening the furnace door half way (to avoid too much heat loss) to allow manual removal of the crucible covers with tools in order to go to the ash cycle. Removal of the covers is necessary in order to burn the coal and then determine the weight of residual ash.

Normally the interior of the furnace is flushed with nitrogen during the moisture and volatiles cycles to avoid oxidation, while the ash cycle is conducted in an oxygen atmosphere to facilitate oxidation of the sample remaining in the crucible after the previous cycles.

In the system of the present invention, after the tare weight of the crucibles have been obtained and the samples introduced and their weight obtained, with the upper and lower carousels in the closed position, the operator places the crucible covers on top of the crucibles, thereby covering the crucibles, and the weight of the covers is obtained by reweighing and the cycle starts by raising the covers automatically and increasing the temperature. The crucibles are reweighed to obtain moisture and the covers are automatically placed on top of the crucibles for volatile analysis and the furnace temperature is again increased and the crucibles are weighed with covers on to obtain volatiles. The covers are then removed automatically to start the ash analysis cycle.

The system of the present invention provides the following advantages over the prior art: safety, no danger of an operator being burned due to manual handling of crucible covers at high temperatures; the convenience of unattended operation; and better reproducibility of the analytical results mostly volatiles because the furnace door never opens during analysis, therefore no air gets inside the furnace that may affect volatile results by oxidation.

The system of the present invention may be applied to any process where the automated covering and uncovering of a series of containers is necessary or useful.

It is understood that the present embodiments described above are to be considered as illustrative and not restrictive. It will be obvious to those skilled in the art to make various changes, alterations and modifications to the invention described herein. To the extent that these variations, modifications and alterations depart from the scope and spirit of the appended claims, they are intended to be encompassed therein.

I claim:

1. An apparatus for automatically covering and uncovering one or more containers as the container is deposited at a station so as to allow the container to be deposited at a station either in an open or closed condition comprising:
   a first carousel for holding one or more containers;
   a second carousel for holding one or more covers for said containers, said first and second carousels sharing a common central axis; and
   means for simultaneously rotating said first and second carousels in unison around their common central axis, while moving the carousels independently along their common central axis.

2. The apparatus of claim 1, wherein the common central axis is vertical and the first carousel is positioned below the second carousel.

3. The apparatus of claim 2, wherein the first and second carousels are positioned such that each container and its respective cover are in alignment.

4. The apparatus of claim 3, wherein individual containers are automatically deposited on a station through movement of the first carousel along its central axis.

5. The apparatus of claim 4, wherein whether a container is open or is closed by a cover is determined by the motion of the second carousel along the common axis of the first and second carousels.

6. The apparatus of claim 1, wherein the first and second carousels are circular.

7. The apparatus of claim 6, wherein the one or more containers are mounted in one or more openings positioned around the perimeter of the first carousel.

8. The apparatus of claim 7, wherein the one or more covers are mounted in one or more openings positioned around the perimeter of the second carousel.

9. The apparatus of claim 8, wherein the presence or absence of a container cover on a container is determined by the motion of the second carousel along the common axis of the first and second carousels.

10. The apparatus of claim 9, wherein said containers are crucibles and where said covers are crucible covers.

11. An apparatus to automatically and simultaneously raise and lower a series of corresponding covers from a series of containers in accord with a predetermined procedure and to deposit any container from said series, covered with said corresponding cover or uncovered, on a station in accord with said predetermined procedure comprising:

a support structure comprising stationary means to permit vertical displacement of a supported body;

a vertically displaceable support body, said body comprising means to communicate with said stationary means to permit vertical displacement;

a first means to raise and lower and support said vertically displaceable support body, with said raising and lowering means supported by said support structure;

an upper means to support a series of said covers in a generally horizontal circular configuration;

a lower means to support a series of said containers in a generally horizontal circular configuration with said means disposed below said upper means;

axle means to support said upper and said lower support means along a common central vertical rotational axis, with said support means able to rotate about said axis, and with said axle supporting means passing through and supported by said vertically displaceable body;

means to rotate said lower support means about said common central vertical axis, with said means supported by said vertically displaceable body;

means to vertically align said upper and said lower supporting means so that each corresponding cover in said series is vertically aligned with a container to which said cover corresponds and with said means also linking said upper and lower supporting means so that both said supporting means rotate synchronously about said common central vertical axis;

a second means to raise and lower said upper support means so that said series of containers can be uncovered or covered and with said second means to raise and lower connected to said vertically displaceable body.

12. The apparatus according to claim 11 wherein said upper support means comprises an upper carousel having a multiplicity of openings to seat said covers and with said multiplicity of openings to seat said covers forming a generally circular pattern and said lower support means comprises a lower carousel having a multiplicity of openings to seat said containers and with said multiplicity of openings to seat said containers forming a generally circular pattern.

13. The apparatus according to claim 12 wherein said lower carousel further comprises a center and said lower carousel has an opening about said center and wherein said upper carousel has a center and wherein said axle means to support said upper and said lower support means comprises a hollow shaft connected around said opening of said lower carousel, and with said shaft protruding downwards from said lower carousel and wherein said axle means to support said upper carousel comprises a rod, said rod having an end and a distal end, and with an end of said rod connected to said center of said upper carousel, with said rod protruding downwards and passing through said opening about said center of said lower carousel and through said hollow shaft and with said distal end connected by connecting means to said second means to raise and lower.

14. The apparatus according to claim 13 wherein said connecting means comprises a rotational coupling and said second means to raise and lower is a pneumatic cylinder.

15. The apparatus according to claim 14 wherein said means to rotate comprises a gear, with said hollow shaft passing through and connected to said gear, with said gear connected to a pulley and said pulley driven by a step motor.

16. The apparatus according to claim 15 wherein said lower carousel further comprises a face, with said face facing said upper carousel, and wherein said means to vertically align said upper and said lower supporting means comprises a pin connected to and protruding perpendicularly upwards from said face of said lower carousel, and an aperture to receive said pin, with said upper carousel having said aperture, and with said pin and said aperture aligned so that with said pin in said aperture, each opening in said upper carousel is vertically aligned with an opening in said lower carousel, and with said pin of sufficient length to remain within said aperture when said upper carousel is moved upwards and wherein said pin received by said aperture links said lower to said upper carousel so that both carousels can rotate synchronously.

17. The apparatus according to claim 16 wherein said second means to raise and lower is a pneumatic cylinder.

18. The apparatus according to claim 17 wherein said hollow shaft further comprises bearings to support said rod and a retaining ring to prevent vertical movement of said hollow shaft within said vertically displaceable support body and said retaining ring further comprises means to signal a position to a sensor.

19. The apparatus according to claim 18 wherein said stationary means to permit vertical displacement of a supported body comprising said support structure comprises a stationary component of a slide joint, and said means to communicate with said stationary means comprising said support body comprises a slide joint component complementary to said stationary component.

20. The apparatus according to claim 19 wherein said covers are crucible covers, and said containers are crucibles, and wherein each crucible cover has an outer perimeter, and each said outer perimeter of each said cover has a ledge projecting therefrom, so that when each cover is seated on said upper carousel each cover ledge keeps each said cover in place, and wherein each crucible has an outer perimeter, and each said outer perimeter of each said crucible has a ledge projecting therefrom, so that when each said crucible is seated on said lower carousel each crucible ledge keeps each said crucible in place.

21. An apparatus to automatically and simultaneously raise and lower a series of corresponding covers from a series of crucibles containing samples, with said covers and said crucibles contained in a furnace, in accord with a predetermined procedure for proximate analysis of said samples, and to deposit any crucible from said series on a balance platform, contained within said furnace, for weight determination, with said any crucible covered with said corresponding cover or uncovered, comprising:
- a support structure comprising stationary means to permit vertical displacement of a supported body;
- a vertically displaceable support body, said body comprising means to communicate with said stationary means to permit vertical displacement;
- a first means to raise and lower and support said vertically displaceable support body, with said raising and lowering means supported by said support structure;
- an upper carousel to support said series of covers, with said upper carousel having a multiplicity of openings in which to seat said series of covers, and with said multiplicity of openings forming a generally circular pattern;
- a lower carousel to support said series of crucibles, with said lower carousel having a multiplicity of openings in which to seat said series of crucibles, and with said multiplicity of openings forming a generally circular pattern and with said lower carousel disposed below said upper carousel;
- axle means to support said upper and said lower carousel along a common central vertical rotational axis, with said carousels able to rotate about said axis, and with said axle supporting means passing through and supported by said vertically displaceable body;
- means to rotate said lower carousel about said common central vertical axis, with said means supported by said vertically displaceable body;
- means to vertically align said upper and said lower carousels so that each corresponding cover in said series is vertically aligned with a crucible to which said cover corresponds and with said means also linking said upper and lower carousels so that both said carousels rotate synchronously about said common central vertical axis;
- a second means to raise and lower said upper carousel so that said series of crucibles can be uncovered or covered, with said second means to raise and lower connected to said vertically displaceable body.

22. The apparatus according to claim 21 wherein said lower carousel further comprises a center and said lower carousel has an opening about said center and wherein said upper carousel has a center and wherein said axle means to support said upper and said lower support means comprises a hollow shaft connected around said opening of said lower carousel, and with said shaft protruding downwards from said lower carousel and wherein said axle means to support said upper carousel comprises a rod, said rod having an end and a distal end, and with an end of said rod connected to said center of said upper carousel, with said rod protruding downwards and passing through said opening about said center of said lower carousel and through said hollow shaft and with said distal end connected by connecting means to said second means to raise and lower.

23. The apparatus according to claim 22 wherein said connecting means comprises a rotational coupling and said second means to raise and lower is a pneumatic cylinder.

24. The apparatus according to claim 23 wherein said means to rotate comprises a gear, with said hollow shaft passing through and connected to said gear, with said gear connected to a pulley and said pulley driven by a step motor.

25. The apparatus according to claim 24 wherein said lower carousel further comprises a face, with said face facing said upper carousel, and wherein said means to vertically align said upper and said lower supporting means comprises a pin connected to and protruding perpendicularly upwards from said face of said lower carousel, and an aperture to receive said pin, with said upper carousel having said aperture, and with said pin and said aperture aligned so that with said pin in said aperture, each opening in said upper carousel is vertically aligned with an opening in said lower carousel, and with said pin of sufficient length to remain within said aperture when said upper carousel is moved upwards and wherein said pin received by said aperture links said lower to said upper carousel so that both carousels can rotate synchronously.

26. The apparatus according to claim 25 wherein said second means to raise and lower is a pneumatic cylinder.

27. The apparatus according to claim 26 wherein said hollow shaft further comprises bearings to support said rod and a retaining ring to prevent vertical movement of said hollow shaft within said vertically displaceable support body and said retaining ring further comprises means to signal a position to a sensor.

28. The apparatus according to claim 27 wherein said stationary means to permit vertical displacement of a supported body comprising said support structure comprises a stationary component of a slide joint, and said means to communicate with said stationary means comprising said support body comprises a slide joint component complementary to said stationary component.

29. The apparatus according to claim 28 wherein each crucible cover comprises an outer perimeter, and each said outer perimeter has a ledge projecting therefrom, so that when each cover is seated on said upper carousel, said ledge comprising said covers keeps each said cover in place, and wherein each crucible comprises an outer perimeter, and each said outer perimeter has a ledge projecting therefrom, so that when each said crucible is seated on said lower carousel said ledge comprising said crucibles keeps each said crucible in place.

* * * * *